(12) United States Patent
Mathys et al.

(10) Patent No.: US 9,155,680 B2
(45) Date of Patent: Oct. 13, 2015

(54) MODULAR FILLING DEVICE FOR AN APPLICATOR

(75) Inventors: Beat Mathys, Zufikon (CH); Ralph Egon Kayser, Lucerne (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 595 days.

(21) Appl. No.: 13/583,451

(22) PCT Filed: Feb. 10, 2011

(86) PCT No.: PCT/CH2011/000023
§ 371 (c)(1),
(2), (4) Date: Sep. 7, 2012

(87) PCT Pub. No.: WO2011/109915
PCT Pub. Date: Sep. 15, 2011

(65) Prior Publication Data
US 2012/0325367 A1   Dec. 27, 2012

(30) Foreign Application Priority Data
Mar. 10, 2010   (CH) .......................................... 331/10

(51) Int. Cl.
*B65B 1/04*      (2006.01)
*A61J 1/20*      (2006.01)
*A61B 17/88*     (2006.01)
*B67B 7/92*      (2006.01)
(Continued)

(52) U.S. Cl.
CPC ........... *A61J 1/2096* (2013.01); *A61B 17/8833* (2013.01); *B67B 7/92* (2013.01); *A61B 2017/00495* (2013.01); *A61J 1/1418* (2015.05); *A61J 1/2058* (2015.05); *A61M 5/1782* (2013.01)

(58) Field of Classification Search
CPC ......... A61M 5/19; A61M 5/1782; A61J 1/20; A61J 1/2096; A61J 1/2058; A61B 17/8833
USPC ............ 141/2, 18, 21–23, 27; 604/82, 86, 87, 604/191
See application file for complete search history.

(56) References Cited

U.S. PATENT DOCUMENTS 5,674,394 A * 10/1997 Whitmore .................. 210/321.8
6,475,183 B1 * 11/2002 Epstein et al. .................. 604/82
(Continued)

FOREIGN PATENT DOCUMENTS

| EP | 1454650 A1 | 9/2004 |
| WO | 96/29113 A1 | 9/1996 |
| WO | 2009/144085 A2 | 12/2009 |

OTHER PUBLICATIONS

International Search Report for PCT/CH2011/000023, dated May 4, 2011.

*Primary Examiner* — Jason K Niesz
(74) *Attorney, Agent, or Firm* — Sughrue Mion, PLLC

(57) ABSTRACT

A modular filling device for filling at least a first reservoir (111) of an applicator (100) with a fluid is proposed. The filling device comprises a container holder (310) with a holding area (320) on which a container (330) is held. The applicator is mounted along a securing direction on an applicator holder (200). In order to permit the greatest possible flexibility in the choice of the container, the container holder (310) can be connected to the applicator holder (200) along a connecting direction that runs transversely with respect to the securing direction for the applicator.

18 Claims, 3 Drawing Sheets

(51) Int. Cl.
*A61M 5/178* (2006.01)
*A61B 17/00* (2006.01)

(56) References Cited

U.S. PATENT DOCUMENTS

| | | |
|---|---|---|
| 6,488,650 B1 | 12/2002 | Epstein et al. |
| 6,610,033 B1 | 8/2003 | Melanson et al. |
| 2002/0087144 A1 | 7/2002 | Zinger et al. |
| 2004/0225274 A1 | 11/2004 | Jansen et al. |
| 2005/0209555 A1 | 9/2005 | Middleton et al. |
| 2007/0079894 A1* | 4/2007 | Kraus et al. .............. 141/319 |
| 2014/0305527 A1* | 10/2014 | Weibel .............. 137/798 |
| 2014/0323970 A1* | 10/2014 | Duncan .............. 604/136 |

* cited by examiner

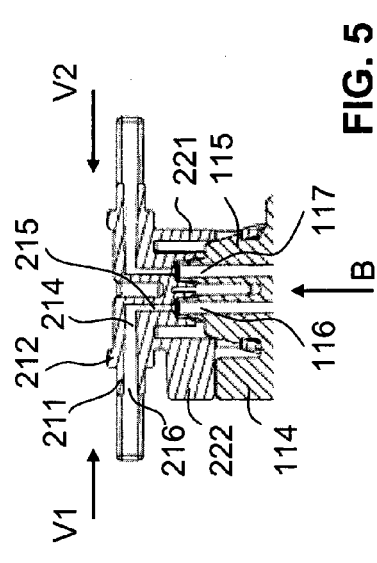
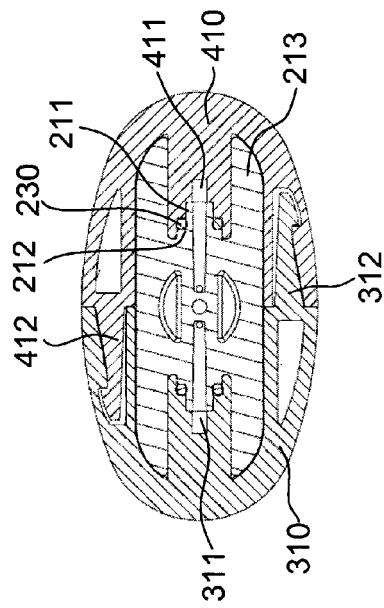
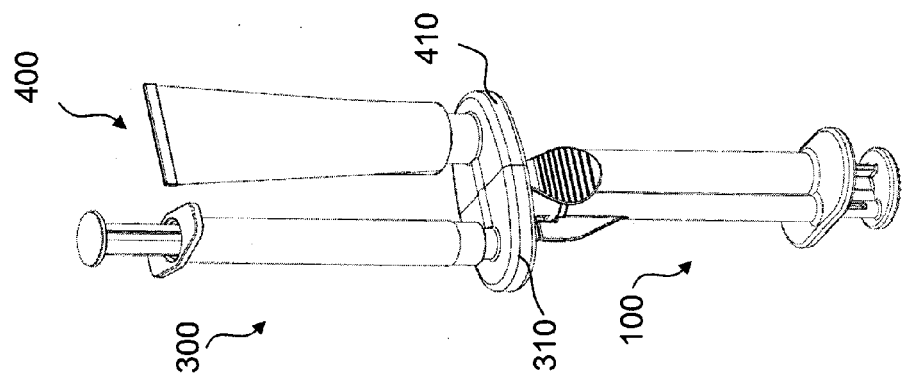
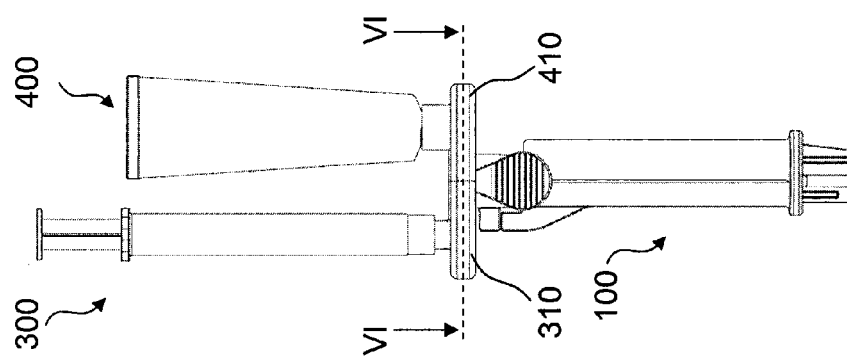

MODULAR FILLING DEVICE FOR AN
APPLICATOR

CROSS REFERENCE TO RELATED APPLICATIONS

This application is a National Stage of International Application No. PCT/CH2011/000023, filed on Feb. 10, 2011, which claims priority from Swiss Patent Application No. 00331/10, filed on Mar. 10, 2010, the contents of all of which are incorporated herein by reference in their entirety.

TECHNICAL FIELD

The present invention relates to a filling device for filling an applicator with at least one fluid. More particularly the invention relates to a modular filling device which, depending on the requirements, allows an applicator to be filled from various types of containers. In accordance with a further aspect, the present invention relates to a set of at least one applicator holder and several container holders, wherein the container holders are designed to hold different types of container.

PRIOR ART

In various applications a mixture of two or more flowable components has to be produced and discharged at a predetermined mixing ratio. One example is the production of an adhesive for technical or medical applications, e.g. a fibrin-based medical adhesive. Another example is the production of a bone cement from several components using a monomer. There are also medicinal products which are produced by mixing two or more components but which cannot be stored in the mixed state. In this case it is desirable to initially store the components separately and only mix them immediately before their administration. Similar tasks also arise in the case of other pharmaceutical or chemical systems of two or more components which are not stable in the mixed state.

From the prior art it is known to hold the components to be mixed in two reservoirs of an applicator, e.g. in the form of a double syringe, and to discharge them through a suitable mixing device. However, it is often problematical to store flowable substances in plastic applicators over a longer period of time, as on the one hand the substances can chemically react with the plastic, and on the other hand there is a risk that gases, more particularly oxygen in the air, can diffuse through the walls of the applicator and chemically modify the contents. This applies in particular to applications in the field of medicine where chemical purity is of special importance.

It is therefore known to store the components to be mixed separately in vials, more particularly glass vials with a septum seal, i.e. in sterilisable glass bottles which are sealed at one end with a self-sealing membrane (known as a septum) that can be punctured in order to remove the components to be mixed from the vials into two separate reservoirs only shortly before application. For this, adapter-like devices are proposed in the prior art which enable the simultaneous filling of two reservoirs from two vials, e.g. the filling devices disclosed in U.S. Pat. No. 6,610,033, U.S. Pat. No. 6,488,650.

WO 2009/144085 also discloses a filling device of this type. Here, two vial holders for one vial each are connected with an applicator holder. An applicator can be inserted into the applicator holder along a fastening direction and can be connected to the applicator holder with Luer connections. The vial holders can be pushed or screwed into the container holders from the opposite side. The applicator can be filled from the vials through fluid connections in the applicator holder. This filling device only allows filling from vials, but not from other types of container.

However, instead of in vials such components can also be held in other containers, e.g. in glass ampoules, i.e. hermetically sealed glass vessels which have to be broken open to remove their containers, or in tubes with a deformable wall area. It is also conceivable to store one of the components in a syringe, as long as the component in question is not too sensitive to ambient influences, and to only take them up in the actual applicator shortly before they are used.

SUMMARY OF THE INVENTION

In accordance with a first aspect the present invention provides a filling device allowing at least one reservoir of an applicator to be filled with a fluid from a container, wherein the device can be adapted to different types of container without essential changes to the design.

A filling device for filling at least one reservoir of an applicator with a fluid from at least a first container is provided, the filling device comprising:

a first container holder with a first holding area, which is designed to hold a first container on the first container holder, wherein the first container holder has a first outlet opening and a fluid channel between the first holding area and the first outlet opening in order to remove a first fluid from the first container through the first outlet opening; and an applicator holder with a fastening area which is designed to detachably fasten an applicator along a fastening direction onto the applicator holder, and wherein the applicator holder has a first inlet opening and a first fluid connection between the first inlet opening and the fastening area in order to take up the first fluid through the first inlet opening into a first reservoir of the applicator; and wherein the first container holder is configured to be connected to the applicator holder along a first connection direction in such a way that the first outlet opening and the first inlet opening are in communication with each other.

In order to facilitate the container holders being able to be designed for very different types of container, e.g. for vials, tubes, syringes, ampoules etc., the first connection direction runs transversely (angled at an angle of more than 45°, preferably more than 60°, particularly preferably essentially perpendicular) to the fastening direction for the applicator. Seen from the applicator the container holder is thus laterally connected to the applicator holder.

Preferably the applicator can be connected to the applicator holder along the fastening direction by means of a simple pushing movement, e.g. via a plug connection. More particularly the applicator can preferably be pushed onto or into the applicator holder. However, for fastening the applicator can carry out a more complex form of movement, e.g. combined pushing and turning, like in a bayonet fitting for example. The translatory part of the movement then defines the fastening direction. The connection of the applicator to the applicator holder is releasable in order to be able to separate the applicator from the applicator holder after filling and to discharge the fluid taken up in the applicator, e.g. by way of an accessory component that is configured to be attached to the applicator, such as a spray nozzle, a mixer etc.

The first container holder is preferably also connectable to the applicator holder by means of a simple pushing movement in the first connection direction. Here too it is preferable that the first container holder is configured to be pushed onto or into the applicator holder. However, in this case as well a more complex movement can be envisaged for fastening, the translatory part of which then defines the first connection direction. The connection between the container holder and applicator holder can be detachable or non-detachable (without destruction).

In the connected state the container holder and applicator holder preferably form an essentially rigid unit. There is therefore no flexible tube connection or suchlike between the container holder and the applicator holder which would make handling more difficult. Naturally the term "rigid unit" does not rule out the container holder or the applicator holder themselves having movable, even flexible parts, e.g. for opening the container. The term "rigid unit" should only indicate that the container holder and applicator are in a defined orientation relative to each other.

The first container holder is in turn designed in such a way that the first container can be applied to the first container holder along a container guide direction which is transverse to the first connection direction and runs essentially anti-parallel to the fastening direction for the applicator when the applicator holder and the first container holder are connected to each other. After connecting the applicator holder to the container holder the filling device is thus preferably handled in the manner familiar to the user, in that the container is applied, e.g. pushed in, pushed onto, screwed in etc. to the filling device in the opposite direction to the applicator. The container can of course already be pre-mounted on the container holder so that for filling the applicator only the entire unit comprising the container holder and container has to be pushed onto the applicator holder.

The container held on the first container holder can be, for example, a syringe with a syringe body with a movable plunger provided therein, a tube with a rigid distal connection area, e.g. in the form of a connecting piece with an external thread and a flexible side wall area, a vial with a closure that can be punctured, more particularly a glass vial with a septum seal, or an ampoule, e.g. a conventional glass ampoule with an ampoule body, tapered neck and ampoule tip that can be broken off. Other types of container are also conceivable, e.g. glass bottles with a screw connection etc. Depending on the container the container holder is designed accordingly. The envisaged purpose of use therefore implicitly also defines the structural design of the container holder within broad limits.

Specifically the applicator holder can, in particular, be designed as follows: the applicator holder comprises a basic body with an upper side and an underside. The fastening area is arranged on the underside of the basic body and can in particular be produced in one piece with the basic body. The first fluid connection has a first inlet section extending from the inlet opening in the basic body essentially along the connection direction, and connected thereto a first outlet section leading to the fastening area, wherein the first outlet section runs at an angle to the first inlet section and extends in the direction of the underside. Preferably the first outlet section essentially extends perpendicularly to the first inlet section and, particularly preferably, runs essentially in the fastening direction.

The basic body is preferably an essentially flat structure, from the underside of which the fastening area projects. Preferably the basic body is of a length in the first connection direction which is at least three times its thickness in the fastening direction. The width perpendicular to these two directions is preferably at least double the height. A basic body of this type allows a compact design. However, other forms of the basic body are of course also possible.

The first container holder can preferably be pushed onto the basic body in the first connection direction in order to connect the first inlet opening with the first outlet opening so that in the mounted position the container holder at least partially surrounds the basic body. It can, however, also be pushed into the basic body for example.

In order to assure a secure and simple fluid connection, the first basic body can at the end of the first inlet section have a first inlet connection piece extending in the first connection direction and forming the first inlet opening. This can then be pushed into the first outlet opening of the first container holder in a first connection direction, wherein the outlet opening in this case is designed to complement the inlet connection piece. In order to assure a seal between the first container holder and the applicator holder an O-ring can be pushed onto the inlet connection piece. Other sealing connections are of course also possible, such as tapered connections.

In order to improve guiding of the container holder on the applicator holder and/or to establish a fixed orientation of the container holder relative to the applicator holder, the basic body can comprise at least one first guide element, e.g. in the form of an elongated lug or a peg, located at a distance from the first inlet connection piece and extending essentially parallel to the first inlet connection piece. A preferably complementary, hollow connection section of the first container holder can then be pushed onto the guide element. In this way the first container holder can be connected with the applicator holder in a defined orientation and is secured against twisting with regard to the applicator holder. Preferably two such guide elements are arranged on opposite sides of the inlet connection piece and engage accordingly in two hollow connection sections of the container holder.

In order to fasten the applicator in the fastening area of the applicator holder, the fastening area can have a holding element, e.g. in the form of a ring, into which a distal end area of the applicator can be pushed and on which a catch structure, e.g. an engaging window, is formed in order to enter into a releasable snap-type connection with a corresponding catch element of the applicator, e.g. an engaging lug. Other types of fastening are of course conceivable, e.g. a normal Luer connection with or without a locking nut.

While the invention also relates to a device for filling an applicator with just one reservoir, the filling device is preferably a device for filling an applicator with two or more parallel reservoirs, e.g. a double or multiple syringe, a cartridge with two or more reservoirs, two detachably connected single syringes etc. In this case the filling device can comprise (at least) a second container holder with a second holding area which is designed to hold a second container on the second container holder. The second container holder then in turn has a second outlet opening and a fluid channel between the second holding area and the first outlet opening in order to remove a second fluid from the second container. Accordingly the applicator holder then also has a second inlet opening and a second fluid connection between the second inlet opening and the fastening area in order to take up the second fluid through the second inlet opening into a second reservoir of the applicator. The second container holder can then be connected with the applicator holder along a second connection direction in such a way that the second outlet opening and the second inlet opening are in communication with each other in order to bring about a connection from the second holding area to the fastening area. The second connection direction is also transverse to the fastening direction for the applicator, preferably in a plane vertical to the fastening direction, particularly preferably antiparallel to the first connection direction.

In the above specific embodiment with a basic body with an upper and underside and a fastening area arranged on the underside, the second fluid connection has a second inlet section essentially extending in the basic body along the second connection direction from the second inlet opening, and connected thereto a second outlet section leading to the fastening area, and the second outlet section runs at an angle to the second inlet section and extends in the direction of the underside. Preferably the first and the second outlet section run essentially parallel to each other and along the fastening direction. The first and the second inlet section preferably lie in a common plane and particularly preferably are collinear to each other, i.e. they are on the same imaginary straight line and point in opposite directions.

In preferred specific embodiments the two container holders can each be pushed onto the applicator holder in order to connect the relevant inlet opening with the relevant outlet opening so that each of the container holders at least partially surrounds the applicator holder. Complementary connection elements can then be formed on the first and second container holder in order to connect the first and second container holder to each other in the mounted state. More particularly this can involve catch elements for a snap-type connection. Therefore, instead of, or in addition, to fixing the container holders on the applicator holder, in this embodiment the two container holders are fixed to each other and are therefore additionally held on the applicator holder.

Especially if the second connection direction runs antiparallel to the first connection direction, the first and the second container holder can each have at least one catch element, which in the mounted state engages in the other container holder, more particularly can be moved into a hollow space thereof, bringing about a snap-type connection between the first and second container holder. Preferably the catch element of the second container holder is then arranged on a side of the applicator holder opposite the catch element of the first container holder.

In a particularly compact and elegant embodiment, in the mounted state the first and second container completely cover the applicator holder towards a side facing away from the fastening area.

In accordance with a further aspect, the present invention provides a modular filling system which allows an applicator to be filled as required from different types of container. Such a filling system comprises an applicator holder of the above-described type and two, three or more container holders designed for holding different types of containers. As indicated above, the container holders can already be pre-fitted with suitable containers.

In other words the present invention provides a set, comprising a filling device of the above type and at least one further container holder, wherein the further container holder is designed for holding a different type of container from the first and/or second container holder. The set can also comprise a suitable applicator.

BRIEF DESCRIPTION OF THE DRAWINGS

Preferred embodiments of the invention are described below with the aid of the drawings, which are only for explanation purposes and must not be interpreted as being limiting. In the drawings:

FIG. 3 shows a side view of a filling device in accordance with the invention;
FIG. 4 shows a perspective view of the filling device of FIG. 3;
FIG. 5 shows a partial view of an enlarged cross-sectional view of the applicator holder of FIG. 2 with the applicator attached thereto;
and
FIG. 6 shows a cross-section through the filling device of FIG. 3 in plane VI-VI.

DESCRIPTION OF PREFERRED EMBODIMENTS

Figure 1:
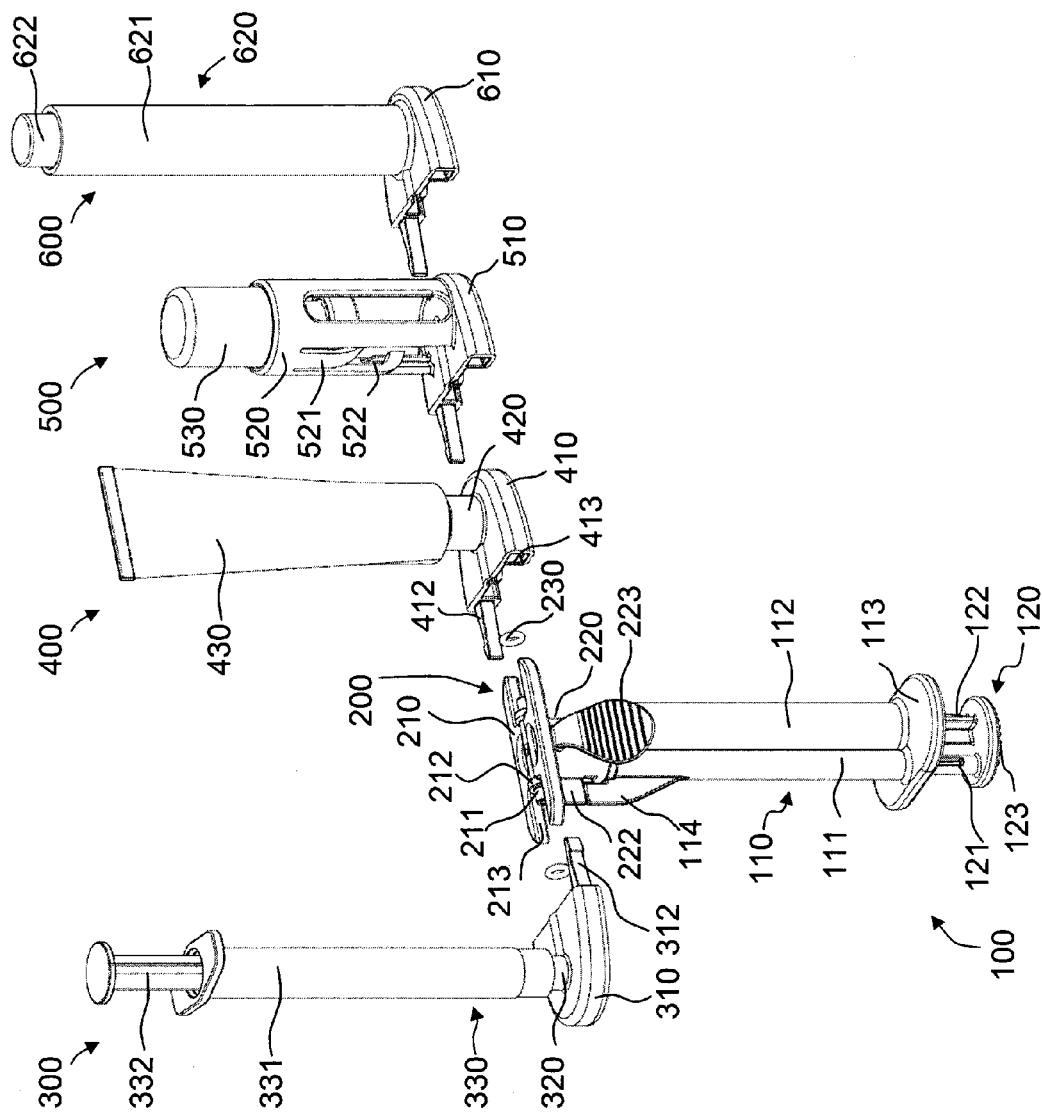
FIG. 1 shows a perspective view of the filling system.
Figure 2:
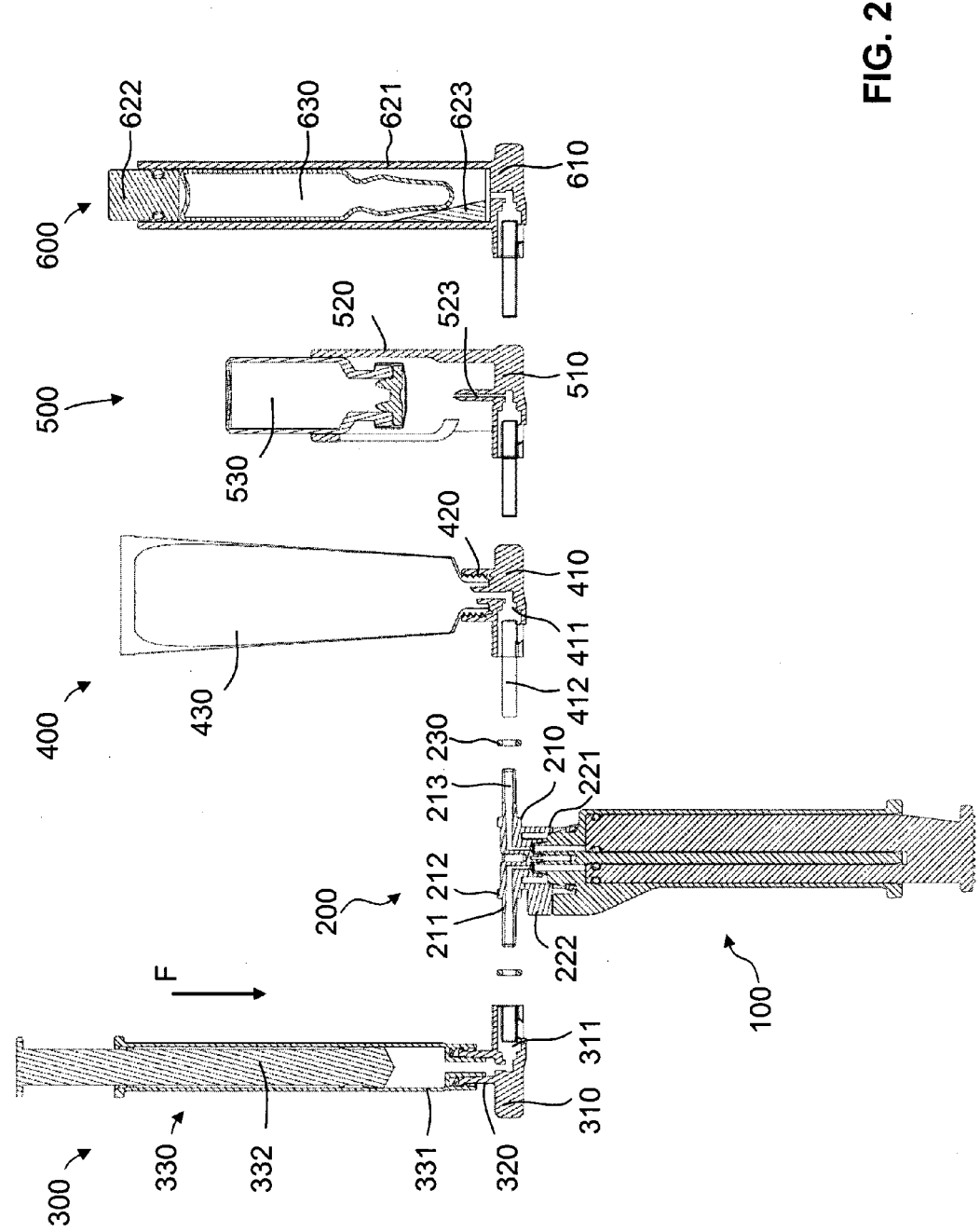
FIG. 2 shows the filling system in FIG. 1 in a central longitudinal section.

In FIGS. 1 and 2 a first exemplary embodiment of a filling system in accordance with the invention is illustrated. Here the system consists of an applicator 100, an applicator holder 200, a first container unit 300, a second container unit 400, a third container unit 500 and a fourth container unit 600.

The applicator 100 is designed as a double syringe. It has an applicator body 110 with two cylindrical, parallel, proximally open reservoirs 111, 112 of the same or (in this case) different diameter and volume. At their distal ends the reservoirs open into two outlets 116, 117 (FIG. 5). A plunger 121, 122 is inserted into each proximal open end of the reservoirs. The two plungers are connected to each other at their proximal ends to form one plunger unit. In this area there is an activation surface 123 for the thumb of a user. A holding flange 113 is for holding the applicator by means of the index and middle finger. To this extent the applicator can be used like a commercially available double syringe.

The applicator holder 200 has a basic body 210 of an elongated, flat, essentially disk-shaped basic form, on the underside of which there is a fastening area 220 for the applicator 100.

The structure of the basic body 210 is best recognised from FIGS. 5 and 6. The basic body 210 has two cylindrical inlet connection pieces 211 which are arranged opposite to each other collinearly on a common longitudinal axis of the basic body. Each of the inlet connection pieces has an axial hole, the open end of which forms an inlet opening 216 and which defines a first inlet section 214 of a fluid connection. The two inlet sections 214 therefore also run collinearly to each other. Each of the inlet sections 214 opens into an outlet section 215, which runs perpendicularly to the inlet section 214, the two outlet sections 215 running parallel to each other downwards and opening into the fastening area 220. Parallel to each of the inlet connections 211, on two sides of each inlet connection there are two guide elements in the form of guide pegs 213, the free ends of which are angled outwards. The guide pegs project axially well beyond the inlet connection 211. An O-ring 230 can be pushed onto each of the inlet connections 211 and in the mounted state is in sealing contact with a circumferential shoulder 212.

The fastening area 220 is designed as follows: each of the outlet sections 215 opens into a conically widening insertion area for the outlets 116, 117 of the applicator 100. The outlets 116, 117 complement the insertion areas and can be inserted into these insertion areas. In order to hold the applicator 100 securely on the applicator holder 200, close to its distal end, adjacent to the outlets 116, 117, the applicator has two webs with engaging lugs 115 on two opposite sides (FIG. 5). The fastening area 220 comprises a cylindrical receiving element 221 which radially surrounds the insertion area and the webs with the engaging lugs 115 and on which two opposite snap-in openings are provided. When the applicator is pushed in, the engaging lugs 115 snap into the snap-in openings of the receiving element 221. This connection between the applicator 100 and the applicator holder 200 essentially functionally corresponds with the connection between a syringe/cartridge and an accessory component described in WO 2007/109915. More particularly, the applicator 100 and the applicator holder 200 have retention means which are designed in accordance with this document.

In order to release the applicator 100 from the applicator holder 200 after filling, the receiving element 221 is elastically deformable so that the snap connection between the engaging lugs 115 and the corresponding snap-in openings can be released again by pressing on a wall area of the receiving element 221 offset by approximately 90° to the snap-in openings in relation to the cylinder axis of the receiving element 221. Through pressing the receiving element 221 is deformed in such a way that the snap-in openings are pushed radially outwards from the engaging lugs 115 and there disengage from the engaging lugs 115. With regard to further details and further possible embodiments of the connection between the applicator and the applicator holder, reference is made to already cited WO 2007/109915, the contents of which are incorporated herein by way of reference for teaching such a connection.

In order to be able to exert this pressure on the receiving element 221 specifically and simply, two press wings 223 which are opposite each other are formed on the basic element 210. The lateral compression of the two press wings 233 is transmitted, offset to the snap-in openings, to the cylindrical receiving element 221 of the fastening area 220 and thereby results in the release of the snap-type connection between the applicator 100 and applicator holder 200.

A coding wing 114 on the applicator 100 and a corresponding coding wing 222 on the applicator holder 200 show the correct orientation of the applicator 100 when connecting it to the applicator holder 200. In addition, the connections themselves are different in order to ensure that the applicator 100 can only be connected correctly orientated.

The first container unit 300 comprises a container holder 310 with an upwardly directed holding area 320 on which a container in the form of a syringe 330 with a syringe body 331 and syringe plunger 332 is held (in this case by means of a conventional Luer lock connection). The container holder 310 has an outer wall, the form of which very roughly corresponds with a half ellipsoid cut along its short axes, which laterally opens towards the applicator holder. The outer wall defines an inner space, in to which, starting from one end of the half ellipsoid a connection area with an outlet opening 311 formed therein extends towards the applicator holder. On one side of the container holder 310 an engaging arm 312, inwardly offset with regard to the outer wall, projects toward the applicator holder. At the free end of the engaging arm there is an engaging lug. A fluid channel angled about 90° connects the holding area 320 with the outlet opening 311.

The second container unit 400 also comprises a container holder 410 with holding area 420 directed upwards. Here the holding area is in the form of a sleeve 420 with an internal thread. A container in the form of a tube 430 with an external thread on a rigid cylindrical connection area is screwed into the holding area 420. With the exception of the holding area 420 the container holder 410 is similar in structure to the container holder 310 and more particularly also comprises an outlet opening 411, a fluid channel connecting the holding area 420 with the outlet opening 411, and an engaging arm 412.

The third container unit 500 also comprises a container holder 510 with a holding area 520 directed upwards, which here is designed in the form of a cylindrical chimney with multiple cutouts. A vial 530 with a septum seal is pushed into the chimney. The vial lies loosely on a first flexible engaging arm 521. By pressing down on the vial the first engaging arm 521 can be elastically pressed outwards via an angled surface formed thereon, and the vial can be brought into a storage position in which, at a distance from a puncturing element in the form of a hollow pin 523, it is in contact with a second engaging arm 522 which extends further downwards than the first engaging arm 521. In this storage position the first engaging arm 521 engages in a tapered section of the vial and thereby prevents the vial from being removed from the chimney. Through renewed downwards pressure with increased force on the vial the second engaging arm 522 can be pressed elastically outwards via an angled surface formed on it so that the vial reaches a removal position, in which the pin punctures the septum seal. The vial is then fixed in the removal position by the second flexible engaging arm 522. In this way it is possible to store a container with a closure that can be punctured on the container holder without the closure being able to be accidentally punctured or the container able to fall out of the holder. In its lower section the container holder 510 is similar in structure to container holder 310.

The fourth container unit 600 again comprises a container holder 610 with an upwardly directed holding area 620 which in this case is designed as an elongated cylindrical chamber 621 with a moveable sealing plunger 622 therein. In the chamber 621 a glass ampoule is 630 is accommodated which through pressing on the plunger 622 can be pushed onto a ramp 623 in order to shear off the tip of the ampoule. Apart from this the container holder 610 is again similar in structure to the container holder 310.

In order to fill both reservoirs 111, 112 the applicator 100 is attached to the applicator holder with the plunger 121, 122 fully inserted. For this the applicator is pushed along a fastening direction B (FIG. 5) into the fastening area 220. The applicator can already be pre-mounted on the applicator holder by the manufacturer.

A container unit is pushed onto each of the two opposite sides of the basic body 210. In the example in FIGS. 3 and 4 these are the first container unit 300 which is pushed on along a first connection direction V1, and the second container unit 400 which is pushed on along a second connection direction V2. The connection directions V1 and V2 are antiparallel to each other, i.e. directed oppositely along the same axis, and perpendicular to the fastening direction B.

When the container holders 310, 410 are pushed on, they surround the basic body 210 from two opposite sides and cover its upper side completely (FIGS. 3 and 4). Towards the bottom too the basic body is largely covered by both container holders in the areas outside the fastening area 220. In the mounted state the two container holders are in contact with each other. The engaging arm 312 of the first container holder 310 projects into a push-in area 413 (FIG. 1) in the interior of the second container holder 410, whereas, inversely, the engaging arm 412 of the second container holder 410 projects into the interior of the first container holder 310. Each of the engaging arms is fixed by its engaging lug in a corresponding recess on the inner side of the outer wall of the other container holder (FIG. 6). In this position each of the inlet connections 211 projects into the corresponding outlet opening 311, 411 of the relevant container holder and is sealed vis-à-vis the container holder by the corresponding O-ring 230. In this way a continuous, externally sealed fluid connection is produced between the syringe 330 and the first reservoir 111 and between the tube 430 and the second reservoir 112.

The plunger unit 120 is then retracted in order to remove the fluids from the two containers 330, 340 separately and simultaneously and to transfer them into the reservoirs 111, 112. Thanks to the compact design of the filling device with short channels only a small quantity of each fluid in the filling device is lost (low dead volume).

By pressing on the press wings 223 the applicator 100 is now released from the filling device. An accessory component, e.g. a mixer or a sprayer, can then be connected to the applicator and the fluids can be discharged from the applicator through the accessory component.

If a fluid is to be taken up into the applicator from a different type of container, instead of the first and/or second container unit 300, 400 a different container unit, e.g. the third or fourth container unit 500, 600 or a container unit with yet another type of container is simply fastened to the applicator holder. In this way the greatest possible freedom in selecting the containers to be used for the components is assured.

For the sake of completeness some additions to the container holder 510 are set out below. Abstractly expressed the container holder 510 provides an example of an adapter-like device for removing a fluid from a container sealed with a closure that can be punctured, which allows the container to be stored on the device without accidentally opening the container. Such a device can be considered as a separate aspect of the present invention, which is independent of the other aspects described above.

In accordance with this aspect a device for removing a fluid from at least one container sealed with a closure that can be punctured, more particularly a vial, is disclosed which comprises:
- a body in which an inlet opening and an outlet opening are formed which are connected by a fluid channel;
- a hollow needle-like puncturing element connected to the inlet opening in order to puncture the closure of the container, more particularly a septum seal when the container is in the removal position; and
- a container holder connected to the body in order to hold the container on the device.

In order to also hold the container securely on the device before puncturing of the closure and to prevent accidental puncturing, the container holder has a first catch structure for fixing the container in a storage position in which the container is further from the basic body than in the removal position (and in which the closure is therefore not already punctured) by way of a releasable snap-type connection. Preferably the container is also fixed in the removal position, and for this the container holder then has a second catch structure to fix the container in the removal position by way of a snap-type connection. The catch structures can interact directly or indirectly with the container. Thus, for example, the container can be pushed directly into the container holder wherein the catch structures directly engage on a corresponding retention structure, e.g. a tapered section of the container, or the container can be held on a separate holder, which can be pushed into or onto the container holder, wherein the catch structures of the container holder interact with a corresponding retention structure of the holder. It is also conceivable that the container holder only has one single catch structure, while the container of the holder has two retention structures, wherein in the storage position the first of these retention structures interacts with the (single) catch structure, while in the removal position the second of these retention structures interacts with the catch structure. Each of the catch structures is preferably designed as follows: the container holder has a preferably at least partially cylindrical defining wall, which can have a single cutout or multiple cutouts. The first catch structure and the second catch structure each have a spring arm formed in the defining wall, at the free end of which an engaging lug is provided which extends into the interior of the defining wall. This makes for a simple and cost-effective manufacturing process. The catch structures are preferably offset with regard to the circumferential direction of the defining wall, e.g. next to each other or offset by approximately 180°, i.e. diametrically opposite each other in order to take up the smallest possible space while retaining the greatest possibly stability of the container holder.

While the invention has been described above with the aid of an exemplary embodiment, the invention is not at all restricted to the above exemplary embodiment, and a large number of modifications are possible. Thus, instead of an applicator of the type set out here, other types of applicator can of course be used, e.g. an applicator as illustrated in WO 2009/144085 or WO 2007/109915. Conventional double syringes or individual syringes combined into a unit can also be used. Accordingly it is also possible to design the applicator connection in a different manner. More particularly, the distances between the outlets of the applicator can be selected differently as required, more particularly as greater than in the exemplary embodiments illustrated here. While the method of fastening the applicator to the applicator holder shown here is advantageous, another type of fastening between the filling device and the applicator can be selected, e.g. a conventional Luer connection. In other embodiments the applicator can only have one reservoir and accordingly only one single container holder is then present. A large number of further modifications are possible.

The invention claimed is:

1. A filling device for filling at least a first reservoir of an applicator with fluid from at least a first container, the filling device comprising:
   a first container holder with a first holding area which is designed to hold a first container on the first container holder, the first container holder having a first outlet opening and a fluid channel between the first holding area and the first outlet opening in order to remove a first fluid from the first container through the first outlet opening; and
   an applicator holder with a fastening area which is designed for fastening an applicator to the applicator holder along a fastening direction, the applicator holder comprising a basic body with an upper side and an underside and having a first inlet opening and a first fluid connection between the first inlet opening and the fastening area in order to take up the first fluid into a first reservoir of the applicator through the first inlet opening, the fastening area being arranged on the underside of the basic body,
   wherein the first container holder is configured to be connected to the applicator holder along a first connection direction in such a way that the first outlet opening and the first inlet opening are in communication with each other, the first connection direction being transverse to the fastening direction for the applicator,
   wherein the first fluid connection has a first inlet section essentially extending along the first connection direction from the first inlet opening and connected thereto a first outlet section leading to the fastening area,
   wherein the first outlet section runs at an angle to the first inlet section and extends toward the underside,
   wherein the at the end of the first inlet section the basic body has a first inlet connection piece, extending in the first connection direction and forming the first inlet opening, the outlet opening of the first container holder being complementary to the first inlet connection piece, and the first inlet connection piece being configured to be pushed into the outlet opening of the first container holder in the first connection direction, wherein at a distance from the first inlet connection piece the basic body has at least one first guide element, essentially extending parallel to the first inlet connection piece, and wherein the first container holder has a complementary hollow connection section configured to be pushed onto the first guide element in order to connect the first container holder to the applicator holder in a defined orientation.

2. The filling device in accordance with claim 1, wherein the first container can be attached to the first container holder along a container guiding direction which runs transversely to the first connection direction and essentially runs antiparallel to the fastening direction for the applicator when the applicator holder and the first container holder are connected to each other.

3. The filling device in accordance with claim 1, wherein the first container holder is designed to hold a syringe, a tube, a vial with a closure that can be punctured, or an ampoule.

4. The filling device in accordance with claim 1, wherein the first container holder is configured to be pushed onto the basic body along the first connection direction in order to connect the first inlet opening to the first outlet opening.

5. The filling device in accordance with claim 1, wherein on the first inlet connection piece a circumferential shoulder is formed and wherein an O-ring is arranged on the first inlet connection piece so that the O-ring adjoins the shoulder.

6. The filling device in accordance with claim 1, wherein the fastening area of the applicator holder has a receiving element into which a distal end area of the applicator can be pushed and on which a catch structure is formed in order to bring about a releasable snap-type connection with a corresponding engaging element of the applicator.

7. A filling device for filling a first and a second reservoir of an applicator with fluid from a first and a second container, the filling device comprising:
- a first container holder with a first holding area which is designed to hold a first container on the first container holder, the first container holder having a first outlet opening and a fluid channel between the first holding area and the first outlet opening in order to remove a first fluid from the first container through the first outlet opening;
- a second container holder with a second holding area which is designed to hold a second container on the second container holder, the second container holder having a second outlet opening and a fluid channel between the second holding area and the second outlet opening in order to remove a second fluid from the second container through the second outlet opening,
- an applicator holder with a fastening area which is designed for fastening an applicator to the applicator holder along a fastening direction, the applicator holder comprising a basic body with an upper side and an underside and having a first inlet opening, a first fluid connection between the first inlet opening and the fastening area in order to take up the first fluid into a first reservoir of the applicator through the first inlet opening, a second inlet opening, and a second fluid connection between the second inlet opening and the fastening area in order to take up the second fluid into a second reservoir of the applicator through the second inlet opening, the fastening area being arranged on the underside of the basic body,
- wherein the first container holder is configured to be connected to the applicator holder along a first connection direction in such a way that the first outlet opening and the first inlet opening are in communication with each other, the first connection direction being transverse to the fastening direction for the applicator,
- wherein the second container holder is configured to be connected to the applicator holder along a second connection direction in such a way that the second outlet opening and the second inlet opening are in communication with each other,
- the second connection direction being transverse to the fastening direction for the applicator,
    - wherein the first fluid connection has a first inlet section in the basic body essentially extending along the first connection direction from the first inlet opening and connected thereto a first outlet section leading to the fastening area,
    - wherein the first outlet section runs at an angle to the first inlet section and extends toward the underside,
    - wherein the second fluid connection has a second inlet section in the basic body essentially extending along the second connection direction from the second inlet opening and connected thereto a second outlet section leading to the fastening area,
    - wherein the second outlet section runs at an angle to the second inlet section and extends toward the underside,
    - wherein the at the end of the first inlet section the basic body has a first inlet connection piece, extending in the first connection direction and forming the first inlet opening, the outlet opening of the first container holder being complementary to the first inlet connection piece, and the first inlet connection piece being configured to be pushed into the outlet opening of the first container holder in the first connection direction,
    - wherein the at the end of the second inlet section the basic body has a second inlet connection piece, extending in the second connection direction and forming the second inlet opening, the outlet opening of the second container holder being complementary to the second inlet connection piece, and the second inlet connection piece being configured to be pushed into the outlet opening of the second container holder in the second connection direction,
    - wherein at a distance from the first inlet connection piece the basic body has at least one first guide element, essentially extending parallel to the first inlet connection piece, and wherein the first container holder has a complementary hollow connection section configured to be pushed onto the first guide element in order to connect the first container holder to the applicator holder in a defined orientation,
    - wherein at a distance from the second inlet connection piece the basic body has at least one second guide element, essentially extending parallel to the second inlet connection piece, and
    - wherein the second container holder has a complementary hollow connection section configured to be pushed onto the second guide element in order to connect the second container holder to the applicator holder in a defined orientation.

8. The filling device in accordance with claim 7, wherein the second connection direction runs antiparallel to the first connection direction.

9. The filling device in accordance with claim 7, wherein the first container holder is configured to be pushed onto the applicator holder along the first connection direction in order to connect the first inlet opening to the first outlet opening, wherein the second container holder is configured to be pushed onto the applicator holder along the second connection direction in order to connect the second inlet opening to the second outlet opening, and wherein complementary connection elements are formed on the first and second container holders in order to connect the first and the second container holders to each other in a mounted state.

10. The filling device in accordance with claim 9, wherein the second connection direction runs antiparallel to the first connection direction and wherein the first and the second container holders each have at least one engaging element which in the mounted state engages in the other container holder and brings about a snap-type connection between the first and the second container holder.

11. The filling device in accordance with claim 9, wherein the first and the second container holders in the mounted state essentially completely cover the application holder towards a side facing away from the fastening section.

12. A set comprising a filling device for filling at least a first reservoir of an applicator with fluid from at least a first container, the filling device comprising:
- a first container holder with a first holding area which is designed to hold a first container on the first container holder, the first container holder having a first outlet opening and a fluid channel between the first holding area and the first outlet opening in order to remove a first fluid from the first container through the first outlet opening; and
  - an applicator holder with a fastening area which is designed for fastening an applicator to the applicator holder along a fastening direction, the applicator holder comprising a basic body with an upper side and an underside and having a first inlet opening and a first fluid connection between the first inlet opening and the fastening area in order to take up the first fluid into a first reservoir of the applicator through the first inlet opening, the fastening area being arranged on the underside of the basic body,
  - wherein the first container holder is configured to be connected to the applicator holder along a first connection direction in such a way that the first outlet opening and the first inlet opening are in communication with each other, the first connection direction being transverse to the fastening direction for the applicator,
  - wherein the first fluid connection has a first inlet section essentially extending along the first connection direction from the first inlet opening and connected thereto a first outlet section leading to the fastening area,
  - wherein the first outlet section runs at an angle to the first inlet section and extends toward the underside,
  - wherein the at the end of the first inlet section the basic body has a first inlet connection piece, extending in the first connection direction and forming the first inlet opening, the outlet opening of the first container holder being complementary to the first inlet connection piece, and the first inlet connection piece being configured to be pushed into the outlet opening of the first container holder in the first connection direction,
  - wherein at a distance from the first inlet connection piece the basic body has at least one first guide element, essentially extending parallel to the first inlet connection piece, and wherein the first container holder has a complementary hollow connection section configured to be pushed onto the first guide element in order to connect the first container holder to the applicator holder in a defined orientation, the set further comprising at least one further container holder, wherein the further container holder is designed for holding a container designed differently from the first container.

13. The filling device in accordance with claim 7, wherein the first container can be attached to the first container holder along a first container guiding direction which runs transversely to the first connection direction and essentially runs antiparallel to the fastening direction for the applicator when the applicator holder and the first container holder are connected to each other, and wherein the second container can be attached to the second container holder along a second container guiding direction which essentially runs parallel to the first container guiding direction when the applicator holder and the second container holder are connected to each other.

14. The filling device in accordance with claim 7, wherein on the first inlet connection piece a first circumferential shoulder is formed and wherein a first O-ring is arranged on the first inlet connection piece so that the first O-ring adjoins the first circumferential shoulder, and wherein on the second inlet connection piece a second circumferential shoulder is formed and wherein a second O-ring is arranged on the second inlet connection piece so that the second O-ring adjoins the second circumferential shoulder.

15. A filling device for filling a first and a second reservoir of an applicator with fluid from a first and a second container, the filling device comprising:
- a first container holder with a first holding area which is designed to hold a first container on the first container holder, the first container holder having a first outlet opening and a fluid channel between the first holding area and the first outlet opening in order to remove a first fluid from the first container through the first outlet opening;
- a second container holder with a second holding area which is designed to hold a second container on the second container holder, the second container holder having a second outlet opening and a fluid channel between the second holding area and the second outlet opening in order to remove a second fluid from the second container through the second outlet opening;
- an applicator holder with a fastening area which is designed for fastening an applicator to the applicator holder along a fastening direction, the applicator holder having a first inlet opening, a first fluid connection between the first inlet opening and the fastening area in order to take up the first fluid into a first reservoir of the applicator through the first inlet opening, a second inlet opening, and a second fluid connection between the second inlet opening and the fastening area in order to take up the second fluid into a second reservoir of the applicator through the second inlet opening,
- wherein the first container holder is configured to be connected to the applicator holder along a first connection direction in such a way that the first outlet opening and the first inlet opening are in communication with each other, the first container holder being configured to be pushed onto the applicator holder along the first connection direction in order to connect the first inlet opening to the first outlet opening, the first connection direction being transverse to the fastening direction for the applicator, wherein the second container holder is configured to be connected to the applicator holder along a second connection direction in such a way that the second outlet opening and the second inlet opening are in communication with each other, the second container holder being configured to be pushed onto the applicator holder along the second connection direction in order to connect the second inlet opening to the second outlet opening, the second connection direction being transverse to the fastening direction for the applicator, and wherein complementary connection elements are formed on the first and second container holders in order to connect the first and the second container holders to each other in a mounted state.

16. The filling device in accordance with claim 15, wherein the second connection direction runs antiparallel to the first connection direction.

17. The filling device in accordance with claim 15, wherein the second connection direction runs antiparallel to the first connection direction and wherein the first and the second container holders each have at least one engaging element which in the mounted state engages in the other container holder and brings about a snap-type connection between the first and the second container holder.

18. The filling device in accordance with claim 15, wherein the first and the second container holders in the mounted state essentially completely cover the application holder towards a side facing away from the fastening section.

* * * * *